United States Patent
Lee

(10) Patent No.: US 9,839,659 B2
(45) Date of Patent: *Dec. 12, 2017

(54) POMEGRANATE EXTRACT CONTAINING LARGE AMOUNT OF ELLAGIC ACID AND USE OF THE POMEGRANATE EXTRACT

(71) Applicants: Hae-Yeon Lee, Gyeonggi-do (KR); HEALTH-LOVE CO., LTD., Hwaseong, Gyeonggi-do (KR)

(72) Inventor: Hae-Yeon Lee, Gyeonggi-do (KR)

(73) Assignees: Hae-Yeon Lee, Uiwang, Gyeonggi-do (KR); HEALTH-LOVE CO., LTD., Hwaseong, Gyeonggi-do (KR)

( * ) Notice: Subject to any disclaimer, the term of this patent is extended or adjusted under 35 U.S.C. 154(b) by 368 days.

This patent is subject to a terminal disclaimer.

(21) Appl. No.: 14/596,778

(22) Filed: Jan. 14, 2015

(65) Prior Publication Data

US 2015/0125556 A1    May 7, 2015

Related U.S. Application Data

(63) Continuation-in-part of application No. 13/639,026, filed on Oct. 2, 2012, now Pat. No. 8,986,749.

(30) Foreign Application Priority Data

Apr. 4, 2014 (KR) .................. 10-2014-0040672

(51) Int. Cl.
 *A61K 36/185* (2006.01)

(52) U.S. Cl.
 CPC ........ *A61K 36/185* (2013.01); *A61K 2236/30* (2013.01)

(58) Field of Classification Search
None
See application file for complete search history.

(56) References Cited

U.S. PATENT DOCUMENTS 8,986,749 B2 * 3/2015 Lee ..................... A61K 36/185
424/725
2005/0202103 A1    9/2005 Rajendran et al.

FOREIGN PATENT DOCUMENTS

JP    2008-542283 A    11/2008
KR    10-2011-0113122    10/2011
WO    WO 2006/127832 A2    11/2006

OTHER PUBLICATIONS

Viuda-Martos, M. et al., "Pomegranate and its Many Functional Components as Related to Human Health: a Review", Comprehensive Reviews in Food Science and Food Safety, vol. 9, 2010, pp. 635-654.
Wang, R. et al., "Pomegranate: Constitutents, Bioactivities and Pharmacokinetics" Fruit, Vegetable and Cereal Science and Biotechnology, 4 (Special Issue 2), pp. 77-87, 2010.
Jimenez et al., "A New Method of Standaritization of Health-Promoting Fruit (*Punica granatum*) Extract," Georgian Medical News, vol. 7, pp. 70-76 (Dec. 31, 2006).
Viuda-Martos, M. et al. "Pomegranate and Its Many Functional Components as Related to Human Health: a Review," Comprehensive Reviews in Food and Science and Food Safety, vol. 9, pp. 635-654, (2010).
Wang, R., et al. "Pomegranate: Constitutents, Bioactivities and Pharmacokinetics," Fruit, Vegetable and Cereal Science an Biotechnology, 4 (Special Issue 2), pp. 77-87, (2010).
Food Engineering Progress, Estrogenic Activity and Physiological Active Components of Iranian Black Pomegranate Seed Extracts, vol. 11, No. 4, pp. 305-312, (Nov. 2007).
Journal of Ethnopharmacology, Pomegranate Extract Improves a Depressive State and Bone Properties in Menopausal Syndrome Model Ovariectomized Mice, vol. 92, pp. 93-101, (Feb. 3, 2004).

\* cited by examiner

*Primary Examiner* — Chris R Tate
*Assistant Examiner* — Randall Winston
(74) *Attorney, Agent, or Firm* — Mintz Levin Cohn Ferris Glovsky and Popeo, P.C.; Kongsik Kim; Linyu Mitra

(57) ABSTRACT

A pomegranate pulp extract is disclosed. The pomegranate pulp extract is effective in treating women's menopausal symptoms, due to the presence of a large amount of ellagic acid. Further disclosed is a method for further improving the treating effect of the pomegranate extract on women's menopausal symptoms. The method includes increasing the content of ellagic acid in the pomegranate extract.

4 Claims, No Drawings

POMEGRANATE EXTRACT CONTAINING LARGE AMOUNT OF ELLAGIC ACID AND USE OF THE POMEGRANATE EXTRACT

CROSS-REFERENCE TO RELATED APPLICATIONS

This application claims priority to Korean Patent Application No. 10-2014-0040672 filed on Apr. 4, 2014 and is a continuation-in-part of U.S. Ser. No. 13/639,026, filed on Oct. 2, 2012, which claims priority to Korean Patent Applications Nos. 10-2010-0032329, 10-2010-0032322 and 10-2010-0072881 filed on Apr. 8, 2010, Apr. 8, 2010 and Jul. 28, 2010, respectively. The applications are incorporated herein by reference.

TECHNICAL FIELD

The present disclosure relates to a particular pomegranate extract, a treating effect of the pomegranate extract on women's menopausal symptoms, and a method for improving the efficacy of the pomegranate extract.

BACKGROUND ART

Estrogen as an endocrine hormone is synthesized in vivo from cholesterol and is secreted from ovarian follicles and corpora lutea. When gonadotropins secreted from the anterior pituitary gland transmit signals to reproductive organs, follicle stimulating hormone (FSH) and luteinizing hormone (LH) regulating the menstrual cycle and enabling pregnancy are secreted and act on the ovaries, where estrogen and progesterone are secreted. Estrogen is a generic name for a group of hormones, including estradiol, estrone and estriol.

Ovaries in premenopausal women are main sources of estrogen. As women reach menopause, their aged ovaries are less likely to respond to hypophyseal gonadotropins (follicle stimulating hormone and luteinizing hormone), leading to a further shortening of the early follicular phase. As a result, the menstrual cycle and the ovulatory phase are more shortened, the production of progesterone is reduced, and the cycle is more irregular. Consequently, the ovarian follicles do not respond to hypophyseal gonadotropins, thus failing to produce estrogen any further. The reduced secretion of estrogen can have major effects on a woman's body, including the genitourinary system. Further, when ovulation stops, this leads to menopause, which signifies the end of menstruation, or the hormone reduction before menopause leads to the occurrence of menopausal symptoms.

The rapidly reduced estrogen in postmenopausal women results in increased dangers of psychological and emotional symptoms, for example, fatigue, excitement, sleeplessness, poor concentration, depression, memory loss, headache, anxiety and nervousness. Other possible dangers include fatigue and excitement resulting from sleep disturbance caused by recurrent facial flushing, intermittent dizziness, paresthesia, tachycardia, pyknocardia, nausea, constipation, diarrhea, arthralgia, myalgia, cold hands and feet, and weight gain. Further, postmenopausal women are very susceptible to osteoporosis and cardiovascular diseases, including heart diseases, hypertension and apoplexy, which are associated with an increase in mortality. Furthermore, changes in integumentary and genitourinary systems are caused, and the possibility of the incidence of autoimmune diseases, cataract and colorectal cancer is increased.

The most effective known method for treating menopausal symptoms, such as facial flushing, is to administer estrogen to women in need of estrogen supplementation.

However, long-term administration of synthetic estrogen may lead to cause serious problems such as the incidence of breast cancer and uterine cancer. Many recent reliable reports have asserted that long-term administration of synthetic estrogen as a hormone replacement therapy increases the possibility of inducing breast cancer. This issue remains highly controversial in all areas of society as well as in research groups. Although the exact cause for the incidence of breast cancer is not clearly demonstrated, the risk of the incidence of breast cancer in women having undergone synthetic estrogen replacement therapy is believed to be associated with estrogen exposure dose with time.

Under these circumstances, considerable research efforts have been directed toward finding phytoestrogen, a kind of vegetable estrogen, as a safer substitute for synthetic estrogen used in hormone replacement therapy. Phytoestrogen refers to a non-steroidal plant compound that exerts estrogenic effects in animals. Most cereals, fruits and vegetables known to have anticancer activity and are effective against heart diseases contain a slight amount of phytoestrogen.

Thus, there is an increasing demand for a safe drug or health functional food that is effective in treating women's menopausal symptoms without causing diseases such as breast cancer and uterine cancer.

SUMMARY OF THE DISCLOSURE

The present disclosure is designed to solve the problems of the prior art, and therefore it is an object of the present disclosure to provide a composition that is effective in treating women's menopausal symptoms.

It is another object of the present disclosure to provide a method for improving the treating effect of a pomegranate extract on women's menopausal symptoms.

According to an embodiment, the method comprises administering to a subject an effective amount of a pomegranate pulp extract, wherein the content of ellagic acid in the pomegranate pulp extract is 1.8-3.2 mg/g. The pomegranate pulp extract may be prepared by a method comprising the steps of (a) adding one or more polysaccharide-degrading enzymes to a pomegranate pulp and (b) concentrating the pomegranate pulp by heating to obtain the pomegranate pulp extract.

The pomegranate pulp extract of the present disclosure is effective in treating women's menopausal symptoms. In addition, according to the method of the present disclosure, the treating effect of the pomegranate extract on women's menopausal symptoms can be improved.

DETAILED DESCRIPTION

In order to achieve the above objects, the present disclosure provides a pomegranate pulp extract containing ellagic acid in an amount that is effective to relieve women's menopausal symptoms.

The content of ellagic acid in the pomegranate pulp extract is preferably at least 0.8 mg/g, more preferably from 1.8 to 3.2 mg/g, more preferably from 2.4 to 3.2 mg/g, even more preferably from 2.7 to 3.2 mg/g.

If the ellagic acid content is less than 0.8 mg/g, the treating effect of the pomegranate pulp extract on menopausal symptoms is negligible. Meanwhile, the ellagic acid content exceeding 3.2 mg/g may increase the risk of side effects, for example, GOT and GPT, which are indicative of liver function, outside their normal ranges.

The present disclosure has been made based on the finding that the use of a pomegranate pulp extract containing a large amount of ellagic acid effectively relieves women's menopausal symptoms. Based on this finding, the present disclosure provides a pomegranate extract containing ellagic acid in an amount that is effective to relieve women's menopausal symptoms, and a method for further improving the treating effect of the pomegranate extract on women's menopausal symptoms by increasing the content of ellagic acid in the pomegranate extract.

Also, based on the finding that the content increase of ellagic acid in a pomegranate extract can provide the excellent effect of treating women's menopausal symptoms, the present disclosure provides a pomegranate extract having a relatively high amount of ellagic acid than the known pomegranate extract on the basis of the same total weight of the extract, thereby exhibiting an equivalent treatment effect on women's menopausal symptoms even by a small intake of the pomegranate extract. In addition, the content increase of ellagic acid in a pomegranate extract can improve the effect of treating women's menopausal symptoms, but it may also increase the content of natural ingredients, particularly polyphenol if the pomegranate extract is simply concentrated so as to raise the content of ellagic acid in the pomegranate extract. Accordingly, such a pomegranate extract may be limited in administration to a polyphenol-sensitive individual.

In order to solve this matter, the present disclosure provides a pomegranate extract containing ellagic acid in an amount of 1.8 to 3.2 mg based on the total weight of the pomegranate extract, thereby exhibiting a sufficient treatment effect on women's menopausal symptoms even by a small administration of the pomegranate extract (preferably a maximum daily dose of the pomegranate extract being 10 ml/day or less) and minimizing the content of polyphenol in the pomegranate extract to allow the administration thereof to a polyphenol-sensitive individual.

As one aspect, the present disclosure provides a method for treating menopausal symptoms in a woman comprising administering to the woman an effective amount of a pomegranate pulp extract, wherein the content of ellagic acid in the pomegranate pulp extract is 1.8-3.2 mg/g, wherein the pomegranate pulp extract is prepared by a method comprising the steps of:

(a) adding one or more polysaccharide-degrading enzymes to a pomegranate pulp; and (b) concentrating the pomegranate pulp by heating to obtain the pomegranate pulp extract. 다.

As used herein, the term "polyphenol" refers to a material having two or more hydroxyl (—OH) groups in a phenol compound formed by substituting one hydrogen of a benzene ring ($C_6H_6$) with a hydroxyl group, and it is known to have good function such as antioxidation but an excessive intake thereof may cause side effects, e.g., damage of liver or kidney.

As used herein, the term "polyphenol-sensitive" refers to highly respond to polyphenol and show a relatively high possibility of side reactions by the intake of polyphenol than an average individual.

The pomegranate extract of the present disclosure provides sufficient effects on the improvement of women's menopausal symptoms and simultaneously minimizes the content of polyphenol, preferably in an amount of 10 to 14 mg, more preferably 10 to 13 mg, most preferably 10 to 12.5 mg, based on the total weight (g) of the pomegranate extract.

Pomegranate is a plant that grows naturally in Southwest Asia, India's northwest province and California, U.S.A. Pomegranates are widely cultivated in subtropical and tropical regions. From ancient times, pomegranates, particularly red pomegranates, have been known as tonic medicinal materials. Particularly, pomegranates are known to be very effective in preventing hypertension and arteriosclerosis. Pomegranates include water-soluble carbohydrates in amounts as large as 38 to 47% and various kinds of vitamins and minerals.

The content of ellagic acid in the pomegranate extract of the present disclosure may vary depending on the production area and harvest time of the pomegranate used, but the ellagic acid content of the final extract of the present disclosure is preferably 0.8 mg/g or more, more preferably 1.8 to 3.2 mg/g, more preferably 2.4 to 3.2 mg/g, most preferably 2.7 to 3.2 mg. In the present disclosure, it is preferred to use a pomegranate of Turkey, a pomegranate of USA, or a mixture thereof. Examples of Turkish pomegranate include Hicaznar pomegranate cv., Cekirdeksiz VI pomegranate cv., Silifke Asisi pomegranate cv., Katirbasi pomegranate cv. and Lefan pomegranate cv., but are not limited thereto. Also, it is preferred to use pomegranate that provides a polyphenol content of 10 to 14 mg, more preferably 10 to 13 mg, most preferably 10 to 12.5 mg based on the total weight (g) of the final pomegranate extract.

The pomegranate extract of the present disclosure is preferably obtained from the pulp of pomegranates.

The content of ellagic acid in the pomegranate extract of the present disclosure is largely differentiated from that of commercially available products. Particularly, comparing with that of U.S. patent application Ser. No. 13/639,026, the pomegranate extract of the present disclosure is different from that of the US application in terms of the content of ellagic acid even though the contents of representative ingredients and the polyphenol ingredient are almost equivalent. By such a difference, although a daily dose of pomegranate extract is restricted in a very small amount, it is believed that the pomegranate extract of the present disclosure can provide the effect of improving women's menopausal symptoms. Also, the content of polyphenol in the pomegranate extract of the present disclosure is little different from that of a pomegranate extract disclosed in U.S. patent application Ser. No. 13/639,026, and thus the pomegranate extract of the present disclosure can achieve an equivalent effect by the administration thereof in a relatively small amount than the pomegranate extract of U.S. patent application Ser. No. 13/639,026, and consequently, the intake of polyphenol contained in the pomegranate extract is considerably reduced, allowing the pomegranate extract to be administered to a polyphenol-sensitive individual.

Accordingly, the present disclosure provides a method for treating women's menopausal symptoms, comprising administering a pomegranate extract containing ellagic acid in an amount of 0.8 mg or more, preferably 1.8 to 3.2 mg based on the total weight (g) of the pomegranate extract, and the pomegranate extract can be administered to a polyphenol-sensitive individual.

The reason for the higher content of ellagic acid in the pomegranate pulp extract of the present disclosure is assumed to be attributed to the kind of the pomegranate as a raw material, the use of the pulp, particular production conditions (for example, concentration temperature, pressure and time conditions of the pomegranate extract), etc., but the present disclosure is not limited thereto.

The pomegranate pulp extract of the present disclosure may be prepared, for example, in accordance with the following method. First, pomegranate fruits are washed. The pomegranate pericarps and seeds are completely removed. One or more kinds of polysaccharide-degrading enzymes, such as pectinase, proteinase, amylase and cellulase, are added to degrade polysaccharides, such as starch, present in the pomegranate. Thereafter, one or more additives, such as gelatin, silicon dioxide, bentonite, silicasol, tannin, cellulose and potassium casseinate, are optionally added to control the physical properties (e.g., turbidity, color and viscosity) of the pomegranate extract, followed by concentration under heating. The pomegranate extract thus obtained contains a particular amount of ellagic acid. Further, an additional filtering step may be added between each of the steps. For example, the filtering process may be carried out at least once after the step of removing the pomegranate pericarps and seeds and before the step of treating a polysaccharide-degrading enzyme, after the step of treating a polysaccharide-degrading enzyme and before the step of concentration, or after the step of concentration.

The pomegranate extract that contains ellagic acid in an amount of 1.8 to 3.2 mg based on the total weight (g) of the pomegranate extract may be prepared according to specific examples comprising the following steps:

S1) removing pericarps and seeds from Turkish pomegranate, American pomegranate or a mixture thereof to obtain only the pomegranate pulp;

S2) sterilizing the pomegranate pulp at 100 to 105° C. for 50 to 80 seconds and then cooling it into 48 to 55° C.;

S3) treating the cooled pomegranate pulp with one or more polysaccharide-degrading enzyme at 48 to 55° C.; and S4) bringing the treated pomegranate pulp into concentration under heating at least twice at high temperature and high pressure of 70 to 100° C. and 400 to 850 mbar, and into concentration under heating at least once at reduced temperature and reduced pressure of 40 to 80° C. and 100 to 350 mbar.

Optionally, at least one filtering step may be carried out in any one of after the S1 step and before the S2 step, after the S3 step and before the S4 step, and after the S4 step.

Each step will be described in detail below.

S1) Step of removing pericarps and seeds from Turkish pomegranate, American pomegranate or a mixture thereof to obtain only the pomegranate pulp The pomegranate pulp extract of the present disclosure does not contain ingredients from the pomegranate pericarps and seeds, which may cause side effects. For example, the pomegranate pericarps contain particular kinds of alkaloids that damage the physical functions of humans and negatively affect the respiratory system and muscles. Addiction to the alkaloids may cause side effects such as seizure, convulsion and narcosis. Other side effects are allergic reactions, such as tongue swelling, that may occur in some persons who take pomegranate seed extracts.

S2) Step of sterilizing the pomegranate pulp at 100 to 105° C. for 50 to 80 seconds and then cooling it into 48 to 55° C. After sequential sterilization, the pomegranate pulp is cooled. The sterilization is preferably carried out at 100 to 105° C. for 50 to 80 seconds, more preferably for 55 to 70 seconds for more rapid treatment. The cooling is preferably carried out at 48 to 55° C.

S3) Step of treating the cooled pomegranate pulp with a starch-degrading enzyme at 48 to 55° C.

The cooled pomegranate pulp is treated with a starch-degrading enzyme. This step is preferably carried out at 48 to 55° C. for 10 to 60 minutes, more preferably at 48 to 55° C. for 20 to 40 minutes. The usuable starch-degrading enzyme is not particularly limited and various starch-degrading enzymes known in the art, including pectinase, proteinase, amylase, cellulase and the like may be used. Among these, pectinase is preferably used.

S4) Step of sequentially bringing the treated pomegranate pulp into concentration under heating at least twice at high temperature and high pressure of 70 to 100° C. and 400 to 850 mbar, and into concentration under heating at least once at reduced temperature and reduced pressure of 40 to 80° C. and 100 to 350 mbar The treated pomegranate pulp is sequentially brought into concentration under heating at high temperature and high pressure and into concentration under heating at reduced temperature and reduced pressure.

Preferably, the concentration under heating at high temperature and high pressure is preferably carried out at least twice, more preferably at least three times, and the concentration under heating at reduced temperature and reduced pressure is preferably carried out at least once, more preferably at least twice, most preferably at least three times.

The concentration under heating at high temperature and high pressure is made under the condition of a temperature of 70 to 100° C. and a pressure of 400 to 850 mbar, the temperature and the pressure may be varied in order (number) of the concentration under heating within said temperature and pressure range, which is included in the scope of the present disclosure. Preferably, a first concentration under heating may be carried out at 70 to 85° C. and 400 to 550 mbar; a second concentration under heating, at 85 to 92° C. and 550 to 750 mbar; and a third concentration under heating, at 92 to 100° C. and 750 to 850 mbar. More preferably, the first concentration under heating may be carried out at 78 to 82° C. and 450 to 500 mbar; the second concentration under heating, at 85 to 90° C. and 600 to 650 mbar; and the third concentration under heating, at 92 to 98° C. and 800 to 850 mbar.

The concentration under heating at reduced temperature and reduced pressure is made under the condition of a temperature of 40 to 80° C. and a pressure of 100 to 350 mbar, the temperature and the pressure may be varied in order (number) of the concentration under heating within said temperature and pressure range, which is included in the scope of the present disclosure. Preferably, a forth concentration under heating may be carried out at 60 to 80° C. and 250 to 350 mbar; and a fifth concentration under heating, at 40 to 60° C. and 100 to 250 mbar. More preferably, the forth concentration under heating may be carried out at 66 to 72° C. and 300 to 330 mbar; and the fifth concentration under heating, at 45 to 55° C. and 100 to 150 mbar.

The pomegranate extract of the present disclosure which contains a large amount of ellagic acid can be applied in various uses including a pharmaceutical composition and a heath functional food. Accordingly, the present disclosure a heath functional food or a pharmaceutical composition for improving women's menopausal symptoms, comprising as an active ingredient a pomegranate extract containing a large amount of ellagic acid.

The pomegranate pulp extract of the present disclosure contains daidzein, genistein, quercetin, estriol and 17β-estradiol, which are representative ingredients of pomegranate extracts. The contents of these ingredients in the pomegranate pulp extract of the present disclosure are almost identical to those in commercially available pomegranate extract products. However, there is a large difference in the content of ellagic acid between the pomegranate pulp extract of the present disclosure and commercially available products. This difference is assumed to bring about an improvement in the relief of menopausal symptoms. Accordingly, the present disclosure provides a composition containing ellagic acid as an active ingredient that is effective in treating women's menopausal symptoms.

Also, besides ellagic acid in large amount, the pomegranate extract of the present disclosure contains polyphenol as a natural ingredient in an equivalent or smaller amount as compared with the known pomegranate extract. Accordingly, the pomegranate extract of the present disclosure can provide the significant effect of improving women's menopausal symptoms even by a maximum daily dose of 10 ml/day or less and can be administered to a polyphenol-sensitive individual.

The pomegranate extract of the present disclosure which contains a large amount of ellagic acid can be applied in various uses including a pharmaceutical composition and a heath functional food.

The present disclosure also provides a health functional food for treating women's menopausal symptoms, including the pomegranate pulp extract or ellagic acid as an active ingredient.

The health functional food of the present disclosure comprises ellagic acid in a large amount and polyphenol in an equivalent or smaller amount as compared with the known pomegranate extract. Accordingly, the health functional food can provide the significant effect of improving women's menopausal symptoms even though the maximum daily dose of the pomegranate extract is 10 ml/day or less, and it can be administered to a polyphenol-sensitive individual. The content of ellagic acid in the pomegranate extract is 1.8-3.2 mg/g and thus the maximum daily dose of ellagic acid in the pomegranate pulp extract may be 18-32 mg/day or less.

The health functional food of the present disclosure may be supplied by filling the single dose thereof in an individual container, and the single dose may contain the pomegranate extract in an amount of 1 to 10 ml, preferably any one of 10 ml, 5 ml, 4 ml, 3 ml, 2 ml or 1 ml, wherein the content of ellagic acid in the pomegranate extract is 1.8-3.2 mg/g. Thus, the single dose may contain the pomegranate extract in an amount of 1 to 10 ml, wherein the content of ellagic acid in the pomegranate extract is 1.8-3.2 mg to 18-32 mg. For example, respectively, 10 ml, 5 ml, 4 ml, 3 ml, 2 ml or 1 ml of the pomegranate extract contains ellagic acid in an amount of 18-32 mg, 9-16 mg, 7.2-12.8 mg, 3.9-9.6 mg, 3.6-9.6 mg, 5.4-6.4 mg or 1.8-3.2 mg. The content of ellagic acid in the pomegranate extract is 1.8-3.2 mg/g and thus the maximum daily dose of ellagic acid in the pomegranate pulp extract may be 18-32 mg/day or less.

In addition to the pomegranate extract, the health functional food of the present disclosure may further include one or more pharmacologically active ingredients and/or additives so long as the objects of the present disclosure are not impaired. Examples of such ingredients and additives include, but are not limited to, *Paeonia japonica, Cornus officinalis, Acanthopanax senticosus, Ganoderma lucidium*, the stem bark of *Fraxinus rhynchophylla, Eucommia ulmoides, Angelica gigas, Gardenia jasminoides, Astragalus membranaceus*, malt, trifoliate orange, vitamin C, fructooligosaccharides, stevioside, purified water, and maltodextrin. These ingredients and additives may be used alone or as a mixture thereof.

For example, the health functional food of the present disclosure may include: water-soluble vitamins, such as thiamine (vitamin $B_1$), riboflavin, ascorbic acid, niacin and vitamin $B_6$; fatty acids, such as myristic acid, palmitic acid, stearic acid, oleic acid and linoleic acid; weak acids, such as glycolic acid and acetic acid; and amino acids, such as 8 essential amino acids, i.e. threonine, valine, methionine, isoleucine, leucine, phenylalanine, tryptophan and lysine, aspartic acid, serine, glutamic acid, proline, glycine, alanine, cysteine, tyrosine, histidine and arginine.

The present disclosure also provides a method for improving the treating effect of the pomegranate extract on women's menopausal symptoms by increasing the content of ellagic acid in the pomegranate extract. In the method of the present disclosure, the content of ellagic acid is preferably adjusted to at least 0.8 mg/g, more preferably from 1.8 to 3.2 mg/g, more preferably from 2.4 to 3.2 mg/g, even more preferably from 2.7 to 3.2 mg/g.

In one embodiment, a daily dose of the pomegranate pulp extract of the present disclosure is preferably from 0.3 to 1 ml/kg body weight. If the daily dose of the pomegranate pulp extract is less than 0.3 ml/kg body weight, the treating effect of the pomegranate pulp extract on menopausal symptoms is negligible. Meanwhile, the daily dose of the pomegranate pulp extract exceeding 1 ml/kg body weight does not contribute to further improvement in the relief of menopausal symptoms when compared to the daily dose of 1 ml/kg weight body. Accordingly, a daily dose of 0.3 to 1 ml/kg weight body is preferred from the view point of in vivo availability and economic efficiency.

According to this embodiment, after the pomegranate pulp extract of the present disclosure is administered daily at a dose of 0.3 to 1 ml/kg body weight, human health indices (for example, red blood cell (RBC) count, blood urea nitrogen (BUN) level, aspartate aminotransferase (AST) level, alanine aminotransferase (ALT) level, creatinine level, glucose level, S-G value, etc.) are maintained within their normal ranges, thus accomplishing the treating effect of the pomegranate pulp extract on menopausal symptoms in a safe manner without causing side effects in humans.

EXAMPLES

The present disclosure will be explained in detail with reference to the following examples. However, these examples may be embodied in various different forms and should not be construed as limiting the scope of the present disclosure. The examples are provided to more fully explain the present disclosure to those having ordinary knowledge in the art to which the present disclosure pertains.

Example 1

1.1 Preparation of Pomegranate Extracts Wherein the Content of Ellagic Acid in the Pomegranate Pulp Extract is 0.8-1.4 mg/g (Preparation of Pomegranate Extracts According to U.S. patent application Ser. No. 13/639,026)

First, foreign matter was removed from pomegranate fruits. Damaged fruits were discarded, and the chosen fruits was washed, cut into pieces, peeled, and pressed under 160 bar to separate the seeds. The pomegranate juice thus obtained was pasteurized. Pectinase was added in an amount of 100-160 g with respect to 6000 L of the pomegranate juice and allowed to stand at 50-60° C. for 1 hr to degrade starch. Gelatin, silicon dioxide and bentonite were added to maintain the turbidity and color of the pomegranate juice and to adjust the viscosity of the pomegranate juice in view of ease of administration. The gelatin and the silicon dioxide were added in amounts of 1200-1800 g and 6000 g, respectively, with respect to 6000 L of the pomegranate juice, and the bentonite was added in an amount of 14 kg with respect to 1000 L of the pomegranate juice. After stirring at 50-60° C. for 30 min, the mixture was filtered under vacuum and concentrated under heating at 55-90° C. for 3 min, 105-110° C. for 90 sec and 100-105° C. for 90 sec to prepare a pomegranate extract containing 0.8-1.4 mg/g of ellagic acid. The pomegranate extract was cooled and pasteurized at 90-94° C. for 20 sec. This procedure was repeated six times. The obtained pomegranate extracts were used as samples in Example 2 below.

1.2 Preparation of Pomegranate Extracts Wherein the Content of Ellagic Acid in the Pomegranate Pulp Extract is 1.8-3.2 mg/g First, foreign matter was removed from 1000 kg of pomegranate fruits. Damaged fruits were discarded, and the chosen fruits was washed, cut into pieces, peeled, and pressed to separate the seeds, thereby obtaining 450 kg of pomegranate pulp. After filtering, the pomegranate pulp was sterilized at 100 to 105° C. for 60 seconds, and then cooled into 48 to 55° C. Pectinase was added in an amount of 70 to 100 ml per 1000 L of pomegranate juice to carry out starch degradation at 48 to 55° C. for 30 minutes. Then, bentonite was added in an amount of 900 g per 1000 L of the pomegranate juice to maintain the turbidity and color of the pomegranate juice and to adjust the viscosity of the pomegranate juice in view of ease of administration. After filtering (1.5 mm and 1 mm) under vacuum, the mixture was sequentially brought into concentration under heating (by 12 brix at 80° C. and 475 mbar, by 17 brix at 87° C. and 626 mbar, by 31 brix at 95° C. and 847 mbar, by 43 brix at 70° C. and 312 mbar, and by 65 brix at 49° C. and 118 mbar, in order). The resultant was again filtered (0.15 m) to prepare a pomegranate extract containing 1.8 to 3.2 mg/g of ellagic acid. The pomegranate extract was aseptically filled, and was packed into a 10 ml individual product. This procedure was repeated six times.

<Example 2> Evaluation of Ellagic Acid Contents of Pomegranate Extracts

The content of ellagic acid in the pomegranate extracts was measured by high-performance liquid chromatography on SP C18 UG 120 (4.6 mm×50 mm, 5 μm) using 0.85% phosphoric acid, a mixed solution of distilled water and methanol (6:4), and pure methanol as mobile phases in a gradient separation mode. Ellagic acid was detected using a UV detector at a wavelength of 370 nm.

Three commercially available products, and the pomegranate extracts prepared in Example 1.1 (corresponding to the pomegranate extracts of U.S. patent application Ser. No. 13/639,026) and Example 1.2 were evaluated for the content of ellagic acid contained therein according to the above method. The results thereof are shown in Table 1. Six samples with different lot numbers were purchased for each of the commercially available products.

TABLE 1

| (Unit: mg/g) | Product A | Product B | Product C | Example 1.1 | Example 1.2 |
|---|---|---|---|---|---|
| Sample No. 1 | 0.21 | 0.39 | 0.27 | 0.80 | 1.80 |
| Sample No. 2 | 0.18 | 0.22 | 0.40 | 0.87 | 2.49 |
| Sample No. 3 | 0.46 | 0.08 | 0.21 | 1.01 | 2.67 |
| Sample No. 4 | 0.19 | 0.13 | 0.27 | 1.40 | 2.82 |
| Sample No. 5 | 0.34 | 0.21 | 0.35 | 1.28 | 2.90 |
| Sample No. 6 | 0.32 | 0.19 | 0.37 | 1.09 | 3.20 |
| Ellagic acid content range | 0.18~0.46 | 0.08~0.39 | 0.21~0.40 | 0.80~1.40 | 1.80~3.20 |

Products A, B and C in Table 1 were purchased from Shadaab Co., Pashapour Trading Co., and Noosh Iran Co., respectively.

As can be seen from Table 1, the pomegranate extracts of Example 1.2 had higher contents of ellagic acid than the commercially available products and that of Example 1.1 (sugar content: 65 brix).

Particularly, comparting the pomegranate extracts on the basis of the content of ellagic acid, the pomegranate extract of Example 1.1 should be administered in a double dose as compared with the pomegranate extract of Example 1.2 for the intake of an equivalent content of ellagic acid.

<Example 3> Evaluation of Polyphenol Contents of Pomegranate Extracts

The content of polyphenol in pomegranate extracts was measured by spectrometry. For this, each sample was dissolved in distilled water and extracted by sonication, and the extract was subject to reaction with a color-developing reagent, followed by quantitative analysis with a spectrometer.

Specifically, 10 mg of tannic acid was put in a 100 ml volume flask and distilled water was filled by the marked line. The standard crude solution was diluted in a proper concentration to obtain a standard solution. To prepare a test solution, 100 mg of the pomegranate extract prepared in Example 1 was put in a 100 ml volume flask and distilled water was filled by the marked line, followed by sofication for dissolution. 7.5 ml of distilled water was taken in test tubes, and the standard solution and the test solution were added in an amount of 1 ml to each test tube. After adding 0.5 ml of the Folin-denis reagent and 1 ml of 35% sodium carbonate in order, each test tube was left in a dark room for 1 hour and the measurement of absorbance was carried out by a UV/Visible Spectrophotometer at 760 nm. The difference between the absorbance of the standard material on concentration and the absorbance of a blank test was used to prepare the analytical calibration curve of the standard material, to which the difference between the absorbance of the pomegranate extract prepared in Example 1 and the absorbance thereof obtained through the blank test was prepared was applied. Thereby, the total amount of polyphenol in the sample was calculated.

Total content of polyphenol (mg/g)=(A×B×C)/D
A: Total Content of Test Solution (mL)
B: Dilution Rate
C: Total Concentration of Polyphenol in Test Solution (mg/mL)
D: Content of Collected Sample (g or mL)

The results are shown in Table 2.

TABLE 2

| (Unit: mg/g) | Example 1.1 | Example 1.2 |
|---|---|---|
| Sample No. 1 | 11.79 | 12.59 |
| Sample No. 2 | 10.59 | 12.67 |

TABLE 2-continued

| (Unit: mg/g) | Example 1.1 | Example 1.2 |
| --- | --- | --- |
| Sample No. 3 | 12.35 | 11.72 |
| Sample No. 4 | 12.89 | 13.21 |
| Sample No. 5 | 13.12 | 11.03 |
| Sample No. 6 | 11.02 | 10.89 |
| Average of Total Polyphenol Content | 11.96 ± 1.01 | 12.01 ± 0.94 |

As can be seen from Table 2, the total contents of polyphenol in the pomegranate extracts of Examples 1.1 and 1.2 were similar Reflecting such results in the ellagic acid content shown in Table 1, it would be understood that the effect of the pomegranate extracts containing ellagic acid in a large amount of 1.80 to 3.20 mg/g according to Example 1.2 does not result from the concentration of the pomegranate extracts.

<Example 4> Evaluation of Relief of Menopausal Symptoms Depending on Ellagic Acid Content 4.1 The pomegranate pulp extract of Example 1.1

An evaluation was made as to what extent the pomegranate pulp extracts containing large amounts of ellagic acid prepared in Example 1.1 relieved women's menopausal symptoms by the following procedure.

Subjects

Through blood tests and Kupperman index, a total of 50 volunteers were publicly selected from postmenopausal women, aged 45-65, who had amenorrhoea of at least 6 months and an FSH value of at least 40. The subjects were divided into 5 experimental groups, 10 subjects per group. Each of the subjects was allowed to take 56 pouches of the pomegranate concentrate over 4 weeks. Specifically, each subject received 20 ml of the pomegranate extract twice daily for 4 weeks. The experimental groups consisted of a control group (70 g of fructooligosaccharide and 13 g of isomerized glucose in purified water), a test group administered with Product A (ellagic acid 0.18-0.46 mg/g), a test group administered with Product B (ellagic acid 0.08-0.39 mg/g), a test group administered with Product C (ellagic acid 0.21-0.40 mg/g), and a test group administered with the extract of Example 1.1 (ellagic acid 0.8-1.4 mg/g). Each subject was allowed to take the pomegranate extract along with 80 ml of water for mouth rinse.

Test Methods

The tests were conducted for a total of 5 weeks. One week prior to administration of the test extracts, the basic information of the volunteers, such as demographic data and past medical history, were recorded. The nutritive conditions, integumentary/mucosal system, otolaryngology system, cardiovascular system, urogenital system, respiratory system, metabolic/endocrine system, digestive system, musculoskeletal system, nervous/mental system and other physical conditions were medically inspected, and whether the results were normal or not was recorded.

According to general exclusion criteria for Kupperman testing, the following subjects were excluded: subjects who suffered from psychogenic menopausal disorders, who had undergone hormone replacement therapy before at least 6 months of testing or were receiving hormone replacement therapy at the time of testing, who suffered from heart diseases (e.g., heart failure, angina or myocardial infarction), who suffered from uncontrollable hypertension, who suffered from malignant tumor, narrow-angle glaucoma or lung disease, and who suffered from severe renal or hepatic dysfunction.

After the pomegranate extracts were distributed for testing, vital signs and concomitant drugs of the volunteers were checked and Kupperman index was evaluated. Drugs and antioxidants causing side effects, such as facial flushing, were restricted. The volunteers were instructed to store and return the pouches after administration to confirm whether they exactly received the drugs. Four weeks after administration, the vital signs, adverse events and concomitant drugs of the volunteers were examined. Then, laboratory examinations were performed.

Kupperman Index Evaluation

General Kupperman index tests were conducted for the evaluation of menopausal symptoms. Immediately before and after administration, an investigator examined the subjects directly, evaluated collectively the occurrence, intensity and frequency of symptoms for Kupperman index parameters, and recorded the scores on the questionnaire. Based on these results, effects of the extracts of Example 1.1 with high contents of ellagic acid were evaluated. The Kupperman index parameters are shown in Table 3.

TABLE 3

| | No symptoms (score 0) | Mild (score 1) | Moderate (score 2) | Severe (score 3) |
| --- | --- | --- | --- | --- |
| Facial flushing | | | | |
| Sweat | | | | |
| Insomnia | | | | |
| Nervousness | | | | |
| Depression | | | | |
| Dizziness | | | | |
| Poor concentration | | | | |
| Joint pain | | | | |
| Headache | | | | |
| Heart palpitation | | | | |
| Colpoxerosis | | | | |

Weighted values were four points for facial flush, two points for sweat, insomnia and nervousness, and one point for depression, dizziness, poor concentration, joint pain, headache, heart palpitation and colpoxerosis. The total score was 51 points.

Test Results (Demographic Information and Kupperman Index Evaluation Results)

The postmenopausal women aged 45-65 were divided into test groups aged 50-53, 54-57, 58-61 and 62-65. Each test group consisted of 10 subjects. The demographic data of the groups are described in Table 4. Kupperman index differences (mean±standard deviation) before and after administration are described in Table 5.

TABLE 4

| | Aged 50~53 | Aged 54~57 | Aged 58~61 | Aged 62~65 |
| --- | --- | --- | --- | --- |
| Control | 2 | 4 | 2 | 2 |
| Product A | 2 | 5 | 2 | 1 |
| Product B | 2 | 4 | 2 | 2 |

TABLE 4-continued

|  | Aged 50~53 | Aged 54~57 | Aged 58~61 | Aged 62~65 |
|---|---|---|---|---|
| Product C | 3 | 3 | 2 | 2 |
| Extract of Example 1.1 | 2 | 4 | 2 | 2 |

TABLE 5

|  | Control | Product A | Product B | Product C | Extract of Example 1.1 |
|---|---|---|---|---|---|
| Kupperman Index | 5.32 ± 0.98 | 8.43 ± 1.09 | 11.87 ± 2.75 | 8.21 ± 2.16 | 25.12 ± 3.48 |

As can be seen from the results in Table 5, the pomegranate pulp extracts containing larger amounts of ellagic acid (ellagic acid 0.8-1.4 mg/g) were much more effective in treating menopausal symptoms than the other pomegranate extracts containing smaller amounts of ellagic acid.

4.2 the Pomegranate Pulp Extract of Example 1.2

An evaluation was made as to what extent the pomegranate pulp extracts containing large amounts of ellagic acid prepared in Example 1.2 relieved women's menopausal symptoms by the following procedure.

Subjects

Through screening tests, volunteers were publicly selected from postmenopausal women, aged 40 to 60, who had amenorrhoea of at least 12 months and an FSH concentration of at least 40 mIU/ml. The subjects decided for their participation in the test after detailed explanation and a full understanding, and made an agreement by letter to comply with precautions for the tests.

One week prior to administration of the test extracts, the basic information of the volunteers, such as demographic data and past medical history, were recorded. The nutritive conditions, integumentary/mucosal system, otolaryngology system, cardiovascular system, urogenital system, respiratory system, metabolic/endocrine system, digestive system, musculoskeletal system, nervous/mental system and other physical conditions were medically inspected, and whether the results were normal or not was recorded.

According to general exclusion criteria for Kupperman testing, the following subjects were excluded: subjects who suffered from psychogenic menopausal disorders, who had undergone hormone replacement therapy before at least 6 months of testing or were receiving hormone replacement therapy at the time of testing, who had amenorrhoea after receiving bilateral ovariectomy or hysterectomy in the last 12 months, who suffered from heart diseases (e.g., heart failure, angina or myocardial infarction), who suffered from uncontrollable hypertension, who suffered from malignant tumor, narrow-angle glaucoma or lung disease, and who suffered from severe renal or hepatic dysfunction.

Test Methods

The tests were conducted for the period of a total of 8 weeks for a total of 60 subjects (30 persons per each group). Experimental groups consisted of a control group (6.5 g of fructooligosaccharide, 1 g of fructose, 0.4 g of red cabbage color, 0.5 g of citric acid, and 0.1 g of pomegranate flavor in purified water), a test group administered with the pomegranate extract of Example 1.2 (ellagic acid 1.8-3.2 mg/g.

After baseline testing, the 60 subjects were randomly assigned in the test group and the control group. All subjects were supplied with the first 4-week test products. The pomegranate extract was administered once in a daily dose of 10 ml/day to the test group. After 4 weeks of administration, the volunteers were instructed to store and return the pouches after administration to confirm whether they exactly received the drugs, and the vital signs, adverse events and concomitant drugs of the volunteers were examined. Then, laboratory examinations were performed (The results are shown as 'second visit' in Table below). Then, all subjects were supplied with the second 4-week test products. The pomegranate extract was administered once in a daily dose of 10 ml/day to the test group. Similar to the first supply, laboratory examinations were performed (The results are shown as 'third visit' in Table below).

Evaluation of Kupperman Index, MRS (Menopause Rating Scale), FSH and Estradiol (E2)

As the first effective evaluation, general Kupperman index tests were conducted for the evaluation of menopausal symptoms and climacteric symptoms. Immediately before and after administration, an investigator examined the subjects directly, evaluated collectively the occurrence, intensity and frequency of symptoms for Kupperman index parameters, and recorded the scores on the questionnaire. Based on these results, effects of the pomegranate extracts of Example 1.2 with high contents of ellagic acid were evaluated.

As the second effective evaluation, the variation of MRS, FSH and estradiol (E2) were confirmed.

The effectiveness was evaluated before/after intake and at visit, the assumption of homogeneity was conducted in independent t-test, the effect assumption before/after intake was conducted in independent t-test at a significant level of 5%, and as the results of the evaluation, the items considered as being not homogeneous was adjusted by the analysis of covariance (ANCOVA). The effect assumption at every visit was analyzed by repeated measure ANOVA (RM ANOVA) at a significant level of 5%.

TABLE 6

First Effectiveness: Variation of KI (total score) at Visit (ITT set)

|  | Pomegranate Extract Group (n = 30) | | | | Placebo Group (n = 30) | | | | |
|---|---|---|---|---|---|---|---|---|---|
|  | Screening | Second Visit | Third Visit | P-value[1] | Screening | Second Visit | Third Visit | P-value[1] | P-value[1] |
| KI (score) | 36.73 ± 5.90 | 22.30 ± 9.55 | 14.67 ± 6.88 | <.0001 | 34.00 ± 7.05 | 28.83 ± 7.76 | 26.52 ± 8.46 | <.0001 | <.0001 |

Values are presented as mean ± SD or number
[1]Analyzed Linear mixed model for repeated measure data

TABLE 7

First Effectiveness: Variation of KI (total score) before/after Intake (ITT set)

| | Pomegranate Extract Group (n = 30) | | | Placebo Group (n = 30) | | | |
|---|---|---|---|---|---|---|---|
| | Screening | Third Visit | P-value[1] | Screening | Third Visit | P-value[1] | P-value[2] |
| KI (score) | 36.73 ± 5.90 | 14.67 ± 6.88 | <.0001 | 34.00 ± 7.05 | 26.52 ± 8.46 | <.0001 | <.0001 |

Values are presented as mean ± SD or number
[1]Analyzed Linear mixed model for repeated measure data
[2]Analyzed by Independent t-test

TABLE 8

Second Effectiveness: Variation of MRS, FSH, E2 at Visit (ITT set)

| | Pomegranate Extract Group (n = 30) | | | | Placebo Group (n = 30) | | | | |
|---|---|---|---|---|---|---|---|---|---|
| | Screening | Second Visit | Third Visit | P-value[1] | Screening | Second Visit | Third Visit | P-value[1] | P-value[1] |
| MRS (score) | 26.13 ± 6.14 | 16.00 ± 6.99 | 10.20 ± 5.03 | <.0001 | 25.90 ± 7.55 | 21.07 ± 6.49 | 18.45 ± 5.82 | <.0001 | <.0001 |
| FSH (mIU/ml) | 84.08 ± 30.60 | 81.98 ± 27.30 | 75.21 ± 23.81 | 0.003 | 91.36 ± 20.64 | 87.57 ± 20.61 | 81.68 ± 17.55 | <.0001 | 0.803 |
| Estradiol (pg/ml) | 6.43 ± 4.68 | 5.19 ± 5.80 | 6.25 ± 9.04 | 0.537[2] | 8.37 ± 6.73 | 5.81 ± 4.74 | 6.18 ± 5.94 | 0.171 | 0.618 |

Values are presented as mean ± SD or number
[1]Analyzed Linear mixed model for repeated measure data
[2]Analyzed by repeated measured ANOVA

TABLE 9

Second Effectiveness: Variation of MRS, FSH, E2 before/after Intake (ITT set)

| | Pomegranate Extract Group (n = 30) | | | Placebo Group (n = 30) | | | |
|---|---|---|---|---|---|---|---|
| | Screening | Third Visit | P-value[1] | Screening | Third Visit | P-value[1] | P-value[1] |
| MRS (score) | 26.13 ± 6.14 | 10.20 ± 5.03 | <.0001 | 25.90 ± 7.55 | 18.45 ± 5.82 | <.0001 | <.0001 |
| FSH (mIU/ml) | 84.08 ± 30.60 | 75.21 ± 23.81 | 0.003 | 91.36 ± 20.64 | 81.68 ± 17.55 | <.0001 | 0.549 |
| Estradiol (pg/ml) | 6.43 ± 4.68 | 6.25 ± 9.04 | 0.893[2] | 8.37 ± 6.73 | 6.18 ± 5.94 | 0.214 | 0.352 |

Values are presented as mean ± SD or number
[1]Analyzed Linear mixed model for repeated measure data
[2]Analyzed by repeated measured ANOVA As can be seen from Tables 6 to 9, the pomegranate pulp extract of Example 1.2 containing larger amounts of ellagic acid was much more effective in treating menopausal symptoms than the control group.

More specifically, from Tables 6 and 7, it was confirmed that the Kupperman indexes of the subjects after 8 weeks were reduced by 50% or more. Further, from Tables 8 and 9, the value of MRS was also dramatically reduced after 8 weeks.

<Example 5> Comparison of Pomegranate Extracts Prepared in Examples 1.1 and 1.2

Kupperman index tests were conducted by using the pomegranate extract of Example 1.1 (sugar content: 65 brix, ellagic acid: 0.80~1.40 mg/g) as the test group in the same manner as Example 3, except that the pomegranate extract was administered once in a daily dose of 40 ml/day.

After 8 weeks, the total scores of Kupperman indexes were evaluated. As a result, KI (total scores) was confirmed to be about 15.08.

Consequently, the pomegranate extracts of Examples 1.1 and 1.2 were confirmed to have similar values of Kupperman index after administration for the same period under the condition that the pomegranate extract of Example 1.2 was administered in a daily dose of 10 ml/day whereas that of Example 1.1, 40 ml/day. That is, the pomegranate extract of Example 1.1 should be administered in an amount of 4 times as much as Example 1.2 so as to provide an equivalent effect of treating menopausal symptoms.

Also, considering Table 2 showing the evaluation results for the polyphenol content, the pomegranate extracts of Examples 1.1 and 1.2 were confirmed to contain polyphenol in a similar amount. Accordingly, in order to provide an equivalent effect of treating menopausal symptoms, the inventive pomegranate extract was administered in a daily dose of 10 ml/day, whereas the pomegranate extract prepared in Example 1.2 should be administered in a daily dose of 40 ml/day, which is 4 times as much as the inventive pomegranate extract. Consequently, the inventive pomegranate extract can provide an equivalent effect by administration in a relative small amount and can reduce the intake of polyphenol, and eventually it can be administered to a polyphenol-sensitive individual.

What is claimed is:

1. A method for treating menopausal symptoms in a woman comprising administering to the woman an effective amount of a pomegranate pulp extract, wherein the content of ellagic acid in the pomegranate pulp extract is 1.8-3.2 mg/g, wherein the pomegranate pulp extract is prepared by a method comprising the steps of:
    (a) adding one or more polysaccharide-degrading enzymes to a pomegranate pulp; and
    (b) concentrating the pomegranate pulp by heating to obtain the pomegranate pulp extract.

2. The method of claim 1, wherein the pomegranate pulp extract is administered in a maximum daily dose of 10 ml/day or less.

3. The method of claim 2, wherein the content of ellagic acid in 10 ml of the pomegranate pulp extract is 18-32 mg.

4. The method of claim 1, wherein the woman is a polyphenol-sensitive individual.

* * * * *